(12) United States Patent
Itamochi et al.

(10) Patent No.: US 10,898,634 B2
(45) Date of Patent: Jan. 26, 2021

(54) REMOVABLE PRESSURE SENSOR AND EXTRACORPOREAL CIRCULATOR PROVIDED WITH REMOVABLE PRESSURE SENSOR

(71) Applicant: TERUMO KABUSHIKI KAISHA, Tokyo (JP)

(72) Inventors: Yosuke Itamochi, Kanagawa (JP); Shinpei Furukawa, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 247 days.

(21) Appl. No.: 15/990,891

(22) Filed: May 29, 2018

(65) Prior Publication Data

US 2018/0272055 A1 Sep. 27, 2018

Related U.S. Application Data

(63) Continuation of application No. PCT/JP2016/071855, filed on Jul. 26, 2016.

(30) Foreign Application Priority Data

Dec. 14, 2015 (JP) .................. 2015-243249

(51) Int. Cl.
*A61M 1/36* (2006.01)
*G01L 9/00* (2006.01)
(Continued)

(52) U.S. Cl.
CPC ........ *A61M 1/3639* (2013.01); *A61M 1/1698* (2013.01); *A61M 1/267* (2014.02);
(Continued)

(58) Field of Classification Search
CPC .................................................. A61M 1/3639
(Continued)

(56) References Cited

U.S. PATENT DOCUMENTS 3,921,622 A * 11/1975 Cole .................. A61M 1/3626
600/437
5,514,102 A 5/1996 Winterer et al.
(Continued)

FOREIGN PATENT DOCUMENTS

DE 3838689 C1 6/1990
EP 181664 A1 8/2007
(Continued)

OTHER PUBLICATIONS

Mihashi et al. Translation of JP2006081852. Published Mar. 2006. Translated Mar. 2020. (Year: 2006).*
(Continued)

*Primary Examiner* — Walter L Lindsay, Jr.
*Assistant Examiner* — Philipmarcus T Fadul
(74) *Attorney, Agent, or Firm* — MacMillan, Sobanski & Todd LLC

(57) ABSTRACT

A removable pressure sensor assembly senses a pressure in an elastically deformable tube conveying blood in an extracorporeal circulator. The assembly includes a main body portion 31 and a pressure measurement element 40 disposed in main body portion 31. Main body portion 31 has a base portion 32 with a tube mounting recessed portion 34 such that an intermediate part of a tube 11 is removably fitted such that tube 11 is elastically deformed. Pressure measurement element 40 is exposed to tube 11 so that it measures a pressure of blood inside tube 11. A lid portion 33 holds tube 11 inside tube mounting recessed portion 34 by selectably closing recessed portion 34 of the base portion. Tube mounting recessed portion 34 has a rectangular cross section, and a width L of the rectangular cross section is set to be smaller than an external dimension D of tube 11.

4 Claims, 7 Drawing Sheets

(51) Int. Cl.
*G01L 7/00* (2006.01)
*A61M 1/26* (2006.01)
*A61M 1/16* (2006.01)
*G01L 17/00* (2006.01)
*G01L 19/04* (2006.01)

(52) U.S. Cl.
CPC ............ *A61M 1/36* (2013.01); *A61M 1/3626* (2013.01); *G01L 7/00* (2013.01); *G01L 9/0027* (2013.01); *G01L 17/005* (2013.01); *G01L 19/04* (2013.01); *A61M 2205/0216* (2013.01); *A61M 2205/3331* (2013.01); *A61M 2205/3368* (2013.01); *A61M 2205/3375* (2013.01)

(58) Field of Classification Search
USPC .......................................................... 73/708
See application file for complete search history.

(56) References Cited

U.S. PATENT DOCUMENTS

| | | | | |
|---|---|---|---|---|
| 8,091,442 | B1* | 1/2012 | Dam | ............... G01N 29/222 73/866.5 |
| 2006/0016743 | A1 | 1/2006 | Ogihara et al. | |
| 2007/0000333 | A1 | 1/2007 | Brugger et al. | |
| 2007/0231203 | A1 | 10/2007 | Mizoguchi et al. | |
| 2008/0098798 | A1* | 5/2008 | Riley | ............... A61M 1/3626 73/19.03 |
| 2009/0078047 | A1* | 3/2009 | Dam | ............... G01N 29/222 73/606 |
| 2009/0118667 | A1* | 5/2009 | Haueter | ............ A61M 5/14244 604/67 |
| 2012/0065596 | A1 | 3/2012 | Haueter et al. | |
| 2012/0082576 | A1* | 4/2012 | Beck | ............... F04B 43/0081 417/474 |
| 2014/0091024 | A1 | 4/2014 | Mizoguchi et al. | |
| 2015/0010433 | A1 | 1/2015 | Takeuchi et al. | |
| 2015/0068670 | A1 | 3/2015 | Mizoguchi et al. | |

FOREIGN PATENT DOCUMENTS

| | | |
|---|---|---|
| JP | 200681852 A | 3/2006 |
| JP | 2013538650 A | 10/2013 |
| WO | 2007123156 A1 | 1/2007 |

OTHER PUBLICATIONS

International Search and Opinion Report, PCT/JP2016/055183, dated Apr. 12, 2016.
International Search Report, PCT/JP2016/071855, dated Aug. 18, 2016.
European Search Report, EP16875145, dated Jun. 17, 2019.

* cited by examiner

REMOVABLE PRESSURE SENSOR AND EXTRACORPOREAL CIRCULATOR PROVIDED WITH REMOVABLE PRESSURE SENSOR

CROSS REFERENCE TO RELATED APPLICATIONS

This application is a continuation of PCT Application No. PCT/JP2016/071855, filed Jul. 26, 2016, based on and claiming priority to Japanese Application No. 2015-243249, filed Dec. 14, 2015, both of which are incorporated herein by reference in their entirety.

BACKGROUND OF THE INVENTION

The present invention relates to a removable pressure sensor which is disposed removably with respect to a tube, through which a liquid such as blood passes, and measures an intra-circuit pressure of the liquid inside the tube, and an extracorporeal circulator provided with the removable sensor.

For example, in a case where cardiac surgery of a patient is performed, an extracorporeal circulator system is used. The extracorporeal circulator system performs extracorporeal blood circulation, auxiliary circulation, and the like in which a pump operates to remove blood from the vein of a patient via a tube, gas in the blood is exchanged or a body temperature is adjusted through an artificial lung, and then the blood returns to the artery or the vein of the patient again via the tube. In order to appropriately perform extracorporeal blood circulation or auxiliary circulation, it is necessary to measure an intra-circuit pressure of a tube of the extracorporeal circulator by using a pressure sensor.

International application WO2007/123156A1 discloses a pressure sensor having a liquid chamber, pressure measurement means, and a liquid flow path. The liquid flow path is formed as a bifurcated portion of a tube by bifurcating a part of the tube of the extracorporeal circulation circuit. The liquid flow path is sealingly connected to a liquid inlet port 40 of the liquid chamber. A liquid passing through the inside of the tube is introduced into the liquid chamber through the liquid flow path, and the liquid flows in along an inner circumference of a side surface of a first connection surface. The liquid chamber has a deformation surface which is deformed when a liquid (blood) is introduced into the liquid chamber, and the pressure measurement means measures a pressure of the liquid by measuring a deformation amount of the deformation surface.

The liquid chamber has a reference surface which is not deformed by a pressure inside the extracorporeal circulation circuit, and the deformation surface which is disposed separately from the reference surface and at least a part of which is deformed by the pressure inside the extracorporeal circulation circuit. Inside the liquid chamber, the reference surface and the deformation surface are interlocked with each other so that a closed liquid-tight space is formed. Accordingly, if a liquid flows into the liquid chamber, a load cell measures the pressure of the liquid inside the extracorporeal circulation circuit based on the deformation of the deformation surface.

In a pressure sensor of an extracorporeal circulation circuit disclosed in WO2007/123156A1, an operator forms a liquid flow path (bifurcated portion) in a middle part of a tube of the extracorporeal circulation circuit and connects the liquid flow path to a liquid chamber when extracorporeal circulation or auxiliary circulation is performed. Then, the operator needs to perform the tasks of connecting the ports of the chamber into the flow path and filling the inside of a liquid flow path and the inside of a liquid chamber with a liquid (e.g., blood). In this way, in order to measure an intra-circuit pressure of a liquid (blood) passing through the tube, in a treatment theater or a surgical theater, an operator needs to perform the tasks of filling the inside of the liquid flow path and the inside of the liquid chamber with the liquid. Therefore, work of measuring the intra-circuit pressure of the liquid (blood) passing through the tube cannot be instantaneously and simply performed by using a pressure sensor in the related art when extracorporeal circulation or auxiliary circulation is being performed.

In addition, the operator needs to interconnect tubing to form the liquid flow path (bifurcated portion) in an intermediate part of the tube as described above. Accordingly, there is concern that an infarcted part of blood or a thrombus of blood is generated in the tube or the liquid flow path. Therefore, an object of the present invention is to provide a removable pressure sensor which can simply, instantaneously, and safely measure an intra-circuit pressure of a liquid circulating in a circuit, and an extracorporeal circulator provided with a removable pressure sensor.

SUMMARY OF THE INVENTION

According to the present invention, there is provided a removable pressure sensor which is removably mounted in an intermediate part of an elastically deformable tube for transferring a liquid. The removable pressure sensor includes a main body portion and a pressure measurement element that is disposed in the main body portion. The main body portion has a base portion which has a tube mounting recessed portion into which the intermediate part of the tube is removably fitted so as to cause the tube to be elastically deformed and to cause a circuit pressure of the liquid inside the tube to be measured by the pressure measurement element; and a lid portion which holds the tube inside the tube mounting recessed portion in a state in which the tube mounting recessed portion of the base portion is closed. A width of a cross section of the tube mounting recessed portion is set to be smaller than an external dimension of the tube.

According to an embodiment of the invention, the pressure measurement element is able to measure the circuit pressure of the liquid inside the tube by only fitting the intermediate part of the tube in the tube mounting recessed portion and causing the tube to be elastically deformed. The width of the cross section of the tube mounting recessed portion is set to be smaller than the external dimension of the tube. Accordingly, the tube mounting recessed portion can form (i.e., compress) the cross-sectional shape of the tube into a shape of being elastically deformed and protruding in accordance with the width of the tube mounting recessed portion. Therefore, the pressure measurement element can simply, instantaneously, and safely measure an intra-circuit pressure of a liquid circulating in a circuit by abutting on a convex portion or a flat surface formed in a part of the deformed tube. That is, in the present invention, since there is no need to fill a liquid flow path, which is a bifurcated portion with respect to the tube, and a separate liquid chamber with a liquid as in the related art. Since there is no bifurcated portion in the tube, a thrombus or the like is not generated. Accordingly, the intra-circuit pressure of the circulating liquid can be safely measured.

Preferably, the tube mounting recessed portion has a rectangular cross section, and a width of the rectangular cross section is set to be smaller than the external dimension of the tube (e.g., the outside diameter of a cylindrical tube). According to an embodiment of the invention, the cross-sectional shape of the tube can elastically deformed to conform with the rectangular cross section of the tube mounting recessed portion. Therefore, the pressure measurement element can simply, instantaneously, and safely measure the intra-circuit pressure of the liquid circulating in the circuit by abutting on a flat conformed surface of the deformed tube. Preferably, the rectangular cross section is a substantially square cross section, and the pressure measurement element is disposed in a position corresponding to the tube which is elastically deformed and is held in the tube mounting recessed portion. Moreover, the tube mounting recessed portion having a substantially square cross section deforms the cross-sectional shape of the tube into a substantially square shape by causing the tube to be elastically deformed in accordance with the substantially square cross section of the tube mounting recessed portion. Therefore, a flat surface can be obtained in a part of the tube, so that the pressure measurement element can accurately measure the intra-circuit pressure of the liquid circulating in the circuit by abutting on the formed flat surface.

Preferably, the removable pressure sensor further includes a temperature sensor that measures a temperature of an environment in which the tube is positioned. A control unit acquires temperature information of the environment from the temperature sensor and the circuit pressure of the liquid inside the tube from the pressure measurement element, and corrects the circuit pressure of the liquid inside the tube measured by the pressure measurement element, in accordance with a value of the temperature. Since the circuit pressure of the liquid inside the tube can be corrected in accordance with the value of the temperature of the environment in which the tube is positioned, even if the temperature of the environment changes, it is possible to acquire a more accurate circuit pressure.

Preferably, the lid portion is attached to the base portion in a manner of being able to be opened and closed, and the lid portion holds the tube inside the tube mounting recessed portion when the lid portion closes the tube mounting recessed portion of the base portion. According to the embodiment, an operator can more simply and instantaneously close the tube mounting recessed portion by using the lid portion, so that the removable pressure sensor can be easily attached and detached at a convenient location at an intermediate part of the flow tube without bifurcating any tubing.

According to the present invention, there is provided an extracorporeal circulator provided with a removable pressure sensor which is removably mounted in a middle part of the elastically deformable tube for transferring a liquid when the liquid is in extracorporeal circulation. The removable pressure sensor includes a main body portion and a pressure measurement element that is disposed in the main body portion. The main body portion has a base portion which has a tube mounting recessed portion into which the middle part of the tube is removably fitted so as to cause the tube to be elastically deformed and to cause a circuit pressure of the liquid inside the tube to be measured by the pressure measurement element; and a lid portion which holds the tube inside the tube mounting recessed portion in a state in which the tube mounting recessed portion of the base portion is closed. The tube mounting recessed portion has a rectangular cross section, and a width of the rectangular cross section is set to be smaller than an external dimension of the tube.

According to an embodiment, the pressure measurement element can measure the circuit pressure of the liquid inside the tube by only fitting the middle part of the tube in the tube mounting recessed portion. The tube mounting recessed portion has a rectangular cross section, and the width of the rectangular cross section is set to be smaller than the external dimension of the tube. Accordingly, the tube mounting recessed portion can form the cross-sectional shape of the tube into a substantially rectangular cross-sectional shape by causing the tube to be elastically deformed in accordance with the rectangular shape of the tube mounting recessed portion. Therefore, the pressure measurement element can simply, instantaneously, and safely measure the intra-circuit pressure of the liquid circulating in the circuit by abutting on the flat surface formed in a part of the tube. That is, in the present invention, since there is no need to fill a liquid flow path, which is a bifurcated portion with respect to the tube, and a liquid chamber with a liquid as in the related art, the intra-circuit pressure of the circulating liquid can be simply and instantaneously measured. Since there is no bifurcated portion in the tube, a thrombus or the like is not generated. Accordingly, the intra-circuit pressure of the circulating liquid can be safely measured.

Thus, the present invention provides a removable pressure sensor which can simply, instantaneously, and safely measure an intra-circuit pressure of a liquid circulating in a circuit, and the extracorporeal circulator provided with a removable pressure sensor.

DESCRIPTION OF PREFERRED EMBODIMENTS

Hereinafter, preferable embodiments of the present invention will be described in detail with reference to the drawings. Since the embodiments described below are suitably specified examples of the present invention, the embodiments are subjected to various limitations which are technically preferable. However, the scope of the present invention is not limited to the aspects thereof unless otherwise stated in the following description particularly limiting the present invention.

First Embodiment

Figure 1:
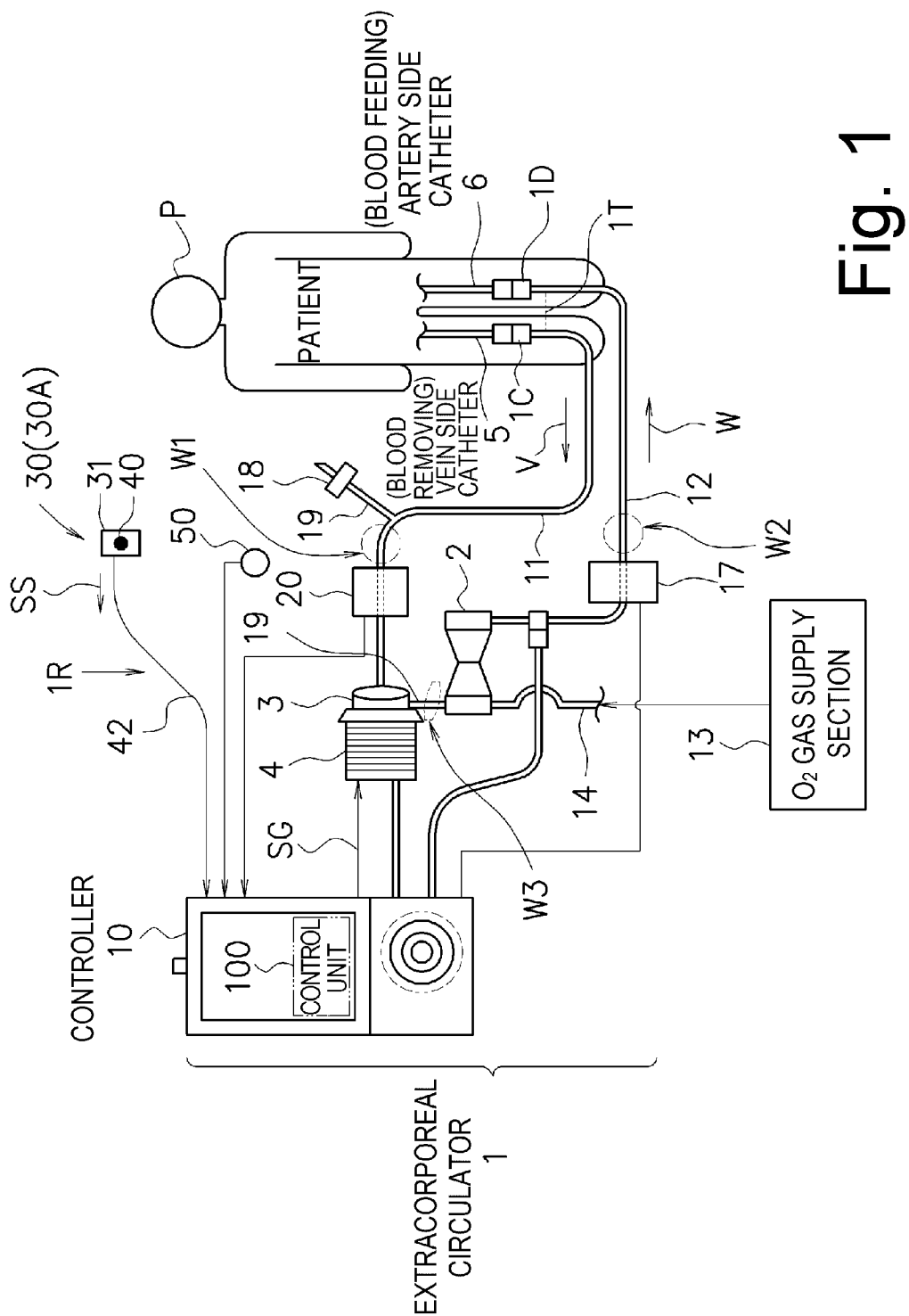
FIG. 1 is a system diagram illustrating an embodiment of an extracorporeal circulator in which a preferable first embodiment of a removable pressure sensor of the present invention is applied.

FIG. 1 is a system diagram illustrating an embodiment of an extracorporeal circulator in which a preferable first embodiment of a removable pressure sensor of the present invention is applied. "Extracorporeal circulation" performed by an extracorporeal circulator 1 illustrated in FIG. 1 includes either an "extracorporeal circulation operation" or an "auxiliary circulation operation". The extracorporeal circulator 1 can perform both the "extracorporeal circulation operation" and the "auxiliary circulation operation" as known in the art.

The "extracorporeal circulation operation" denotes a circulation operation of blood and a gas exchange operation (oxygenation and/or carbon dioxide removal) with respect to the blood performed by the extracorporeal circulator 1 in a case where blood circulation in the heart is temporarily stopped due to cardiac surgery, for example. In addition, the "auxiliary circulation operation" denotes a circulation operation of blood and a gas exchange operation with respect to the blood which are also performed by the extracorporeal circulator 1 in a case where the heart of a patient P that is an application target of the extracorporeal circulator 1 cannot sufficiently function or in a state in which the lung cannot sufficiently perform gas exchange.

In the extracorporeal circulator 1 illustrated in FIG. 1, for example, in a case where cardiac surgery of the patient is performed, a pump of the extracorporeal circulator 1 is operated to remove blood from the vein of the patient, and the blood is oxygenated by exchanging gas in the blood through an artificial lung 2. Thereafter, it is possible to perform artificial lung extracorporeal blood circulation in which the blood returns to the artery or the vein of the patient again. The extracorporeal circulator 1 is an apparatus which operates on behalf of a heart and lungs. As illustrated in FIG. 1, the extracorporeal circulator 1 has a circulation circuit 1R which causes blood to circulate. The circulation circuit 1R includes the artificial lung 2, a centrifugal pump 3, a drive motor 4 which is driving means for driving the centrifugal pump 3, a vein side catheter (blood removing catheter) 5, an artery side catheter (blood feeding catheter) 6, and a controller 10 which serves as a control unit. In addition, the extracorporeal circulator 1 includes a removable pressure sensor 30.

As illustrated in FIG. 1, the vein side catheter (blood removing catheter) 5 is inserted through the femoral vein, and a distal end of the vein side catheter 5 indwells in the right atrium. The artery side catheter (blood feeding catheter) 6 is inserted through the femoral artery. The vein side catheter 5 is connected to the centrifugal pump 3 by using a blood removing tube (also referred to as a blood removing line) 11. The blood removing tube 11 is a conduit line for sending blood. When the drive motor 4 operates the centrifugal pump 3 in response to a command SG of the controller 10, the centrifugal pump 3 removes blood through the blood removing tube 11 and causes the blood to pass through the artificial lung 2. Thereafter, the centrifugal pump 3 can cause the blood to return to the patient P via a blood feeding tube 12 (also referred to as the blood feeding line).

The artificial lung 2 is disposed between the centrifugal pump 3 and the blood feeding tube 12. The artificial lung 2 performs a gas exchange operation (oxygenation and/or carbon dioxide removal) with respect to blood. The artificial lung 2 is a membrane-type artificial lung, for example. It is particularly preferable to use a hollow fiber membrane-type artificial lung. Oxygen gas is supplied to the artificial lung 2 from an oxygen gas supply section 13 through a tube 14.

The blood feeding tube 12 is a conduit line connecting the artificial lung 2 and the artery side catheter 6 to each other. As the blood removing tube 11 and the blood feeding tube 12, it is possible to use conduit lines made of synthetic resin, for example, vinyl chloride resin or silicone rubber which is highly transparent and flexible to be elastically deformable. Blood (liquid) flows in a V-direction inside the blood removing tube 11, and blood flows in a W-direction inside the blood feeding tube 12.

In the example of the circulation circuit 1R illustrated in FIG. 1, an ultrasound air bubble detection sensor 20 is disposed outside the blood removing tube 11 in a middle part of the blood removing tube 11. A fast clamp 17 is disposed outside the blood feeding tube 12 in an intermediate position of the blood feeding tube 12. In a case where the ultrasound air bubble detection sensor 20 detects that an air bubble is present in blood being sent to the inside of the blood removing tube 11, the ultrasound air bubble detection sensor 20 transmits a detection signal of air bubble detection to the controller 10. Accordingly, the fast clamp 17 urgently closes the blood feeding tube 12 in response to a command of the controller 10 in order to stop blood from being sent to the patient P side.

In the ultrasound air bubble detection sensor 20, in a case where an air bubble is incorporated into the circuit due to an erroneous operation of a three-way stopcock 18, damage to the tube, or the like during a blood circulation operation, the incorporated air bubble can be detected. If an air bubble is detected, the controller 10 in FIG. 1 sounds an alarm for notification, reduces the rotational frequency of the centrifugal pump 3, or stops the centrifugal pump 3. Moreover, the controller 10 commands the fast clamp 17 such that the fast clamp 17 immediately closes the blood feeding tube 12 and the air bubble is stopped from being sent to the inside of the body of the patient P. Accordingly, the circulation operation of blood in the circulation circuit 1R of the extracorporeal circulator 1 is temporarily halted to prevent an air bubble from being incorporated into the body of the patient P.

Figure 2:
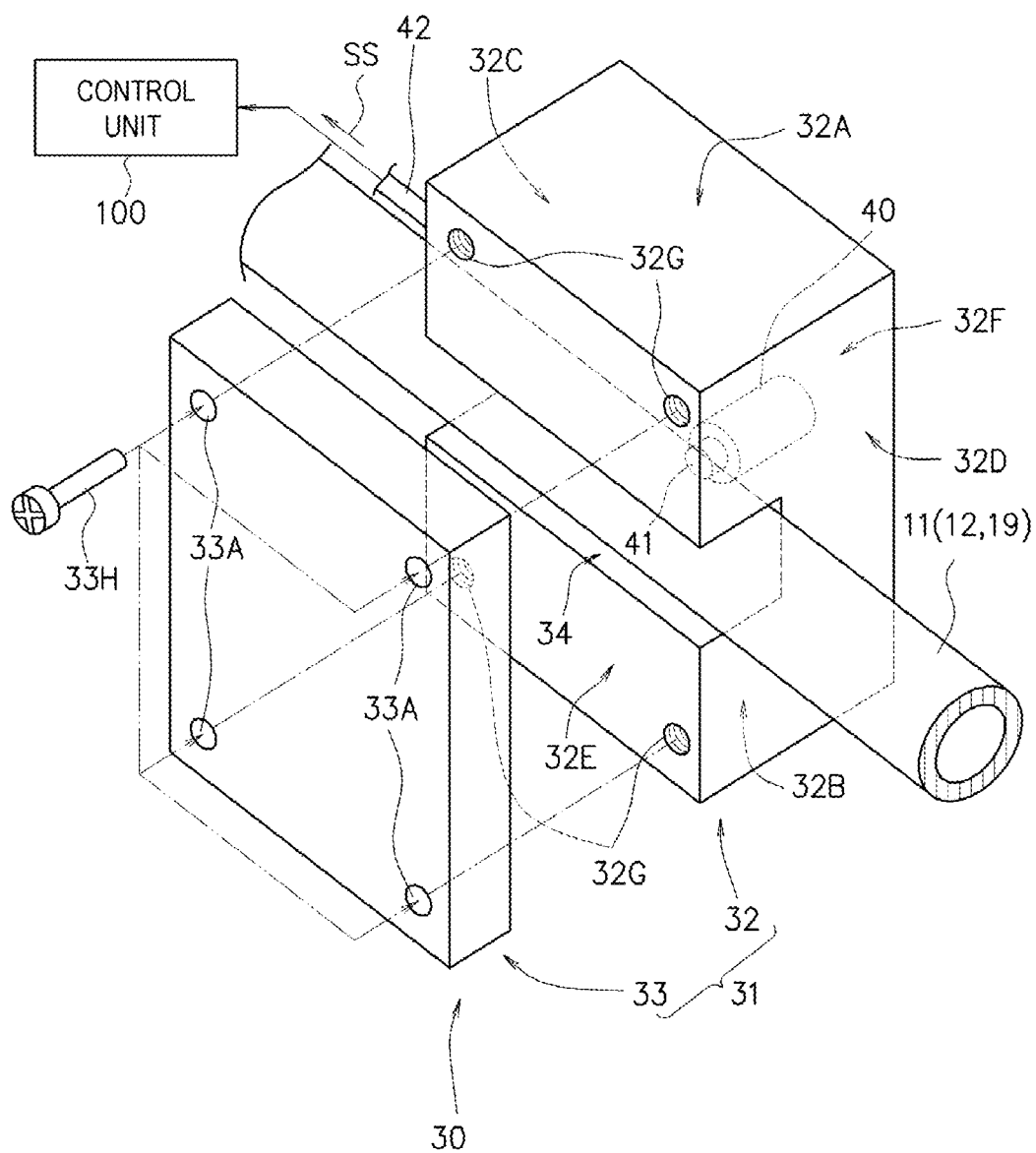
FIG. 2 is an exploded perspective view illustrating the removable pressure sensor of the first embodiment of the present invention.

FIG. 2 is an exploded perspective view illustrating an example of the removable pressure sensor 30 illustrated in FIG. 1. The removable pressure sensor 30 illustrated in FIG. 2 can be removably mounted in any location along the tube of the circulation circuit 1R of the extracorporeal circulator 1 illustrated in FIG. 1. The removable pressure sensor 30 can be mounted on the tube 11 (12, 19), as described below. Accordingly, when the extracorporeal circulator 1 performs an extracorporeal circulation operation or an auxiliary circulation operation with respect to the patient P, the removable pressure sensor 30 can simply, instantaneously, and safely measure the intra-circuit pressure during blood circulation through the inside of the tube 11 (12, 19) in an invasive manner without being in contact with blood.

The following is an example of positions for any location in the tube of the circulation circuit 1R in which the removable pressure sensor 30 illustrated in FIG. 2 can be removably mounted. As shown in FIG. 1 for example, the removable pressure sensor 30 can be removably mounted in any one or all of a mounting position W1 in an intermediate part of the blood removing tube 11 of the circulation circuit 1R, a mounting position W2 in an intermediate part of the blood feeding tube 12 of the circulation circuit 1R, and amounting position W3 in an intermediate part of a connection tube 19 which connects the centrifugal pump 3 and the artificial lung 2 to each other.

The removable pressure sensor 30 is mounted in the mounting position W1 in an intermediate part of the blood removing tube 11 of the circulation circuit 1R. When an extracorporeal circulation operation or an auxiliary circulation operation is performed, it is possible to simply, instantaneously, and safely measure the intra-circuit blood removing pressure during blood circulation through the inside of the blood removing tube 11 without being in contact with blood. Accordingly, when blood is removed from the patient P via the blood removing tube 11, the controller 10 can determine a trend of a change in a blood removing state (tendency of a change in pressure) of the patient P in the blood removing tube 11. In addition, the removable pressure sensor 30 is mounted in the mounting position W2 in an intermediate part of the blood feeding tube 12 of the circulation circuit 1R. When an extracorporeal circulation operation or an auxiliary circulation operation is performed, it is possible to simply, instantaneously, and safely measure the intra-circuit blood feeding pressure during blood circulation through the inside of the blood feeding tube 12 without being in contact with blood. Accordingly, when blood is fed into the patient P via the blood feeding tube 12, the controller 10 can determine an unfavorable condition of the artificial lung 2 or a trend of a change in a blood feeding state (tendency of a change in pressure) of the patient P in the blood feeding tube 12.

Moreover, the removable pressure sensor 30 is mounted in the mounting position W3 in an intermediate part of the connection tube 19. When an extracorporeal circulation operation or an auxiliary circulation operation is performed, it is possible to simply, instantaneously, and safely measure the intra-circuit blood feeding pressure during blood circulation through the inside of the connection tube 19 without being in contact with blood when blood is fed by the centrifugal pump 3 via the connection tube 19. Accordingly, the controller 10 can detect a trend of a change in an operation (tendency of a change in pressure) of the centrifugal pump 3 in the circulation circuit 1R. In this way, an operator can removably mount the removable pressure sensor 30 in any position such as the mounting positions W1, W2, and W3 of the circulation circuit 1R, and a control unit 100 of the controller 10 can detect a trend of a change in the intra-circuit pressure (tendency of a change in pressure) of blood in the blood removing tube 11 (the blood feeding tube 12 and the connection tube 19) configuring the circulation circuit 1R, by receiving an intra-circuit pressure signal SS from the removable pressure sensor 30 via a signal line 42.

For example, the removable pressure sensor 30 illustrated in FIG. 2 has a structure capable of being removably mounted in the same manner in any position of the mounting position W1 in an intermediate part of the blood removing tube 11 of the circulation circuit 1R illustrated in FIG. 1, the mounting position W2 in an intermediate part of the blood feeding tube 12 of the circulation circuit 1R, and the mounting position W3 in an intermediate part of the connection tube 19 which connects the centrifugal pump 3 and the artificial lung 2 to each other. The blood removing tube 11, the blood feeding tube 12, and the connection tube 19 are made of the same material and have the same tube outer diameter (external dimension). As described above, the blood removing tube 11, the blood feeding tube 12, and the connection tube 19 are conduit lines made of a synthetic resin, for example, vinyl chloride resin or silicone rubber which is highly transparent and flexible to be elastically deformable.

The removable pressure sensor 30 illustrated in FIG. 2 has a main body portion 31 and a pressure measurement element 40 which is attached to the main body portion 31. The main body portion 31 has a base portion 32 and a lid portion 33. For example, the base portion 32 is a rectangular parallelepiped solid member and has a tube mounting recessed portion 34 formed as a channel or groove. The base portion 32 has an upper surface 32A, a lower surface 32B, right and left side surfaces 32C and 32D, a front surface 32E, and a rear surface 32F. The tube mounting recessed portion 34 is formed from the front surface 32E side to a position in the middle toward the rear surface 32F side. The tube mounting recessed portion 34 is formed from the left side surface 32C side leading to the right side surface 32D.

Figure 3:
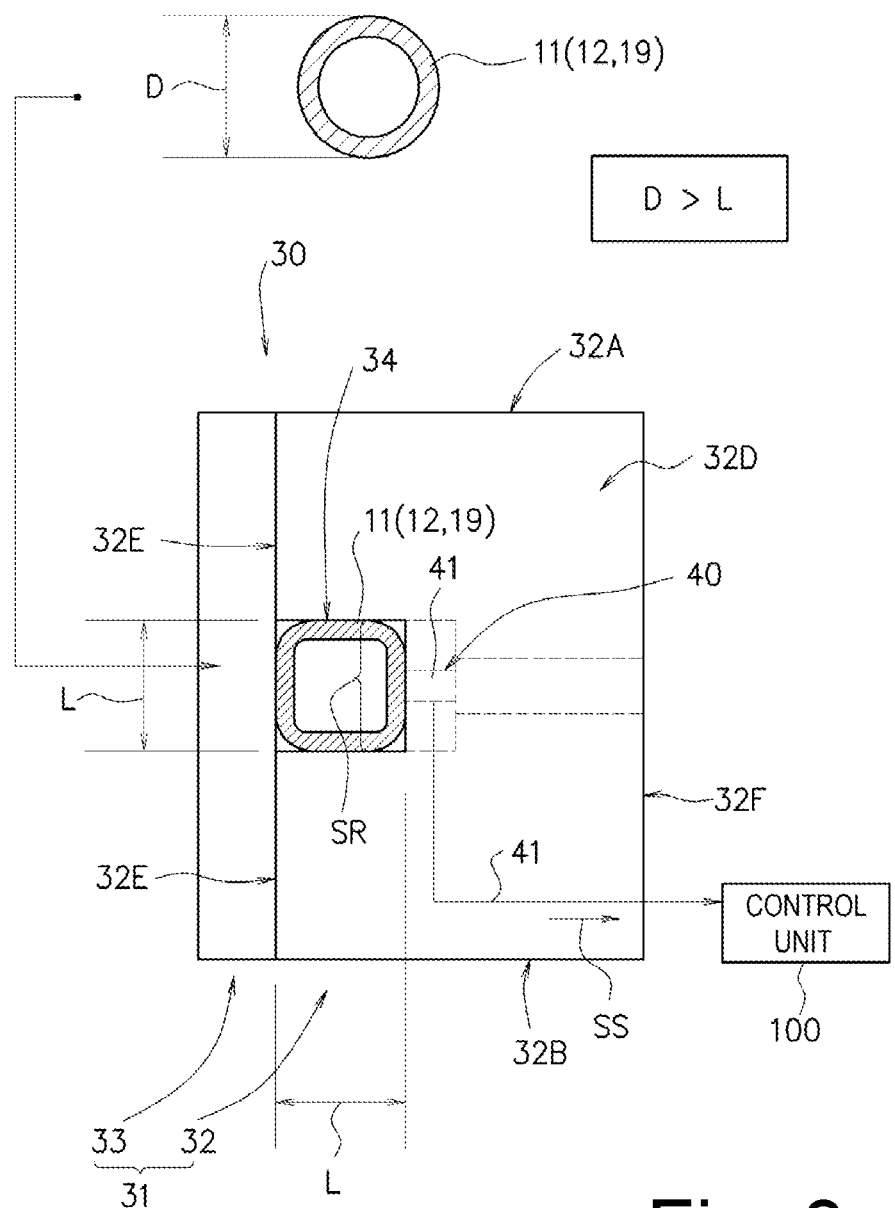
FIG. 3 is a SIDE view illustrating a main body portion illustrated in FIG. 2, and a shape of a blood removing tube (a blood feeding tube and a connection tube).
Figure 4A:
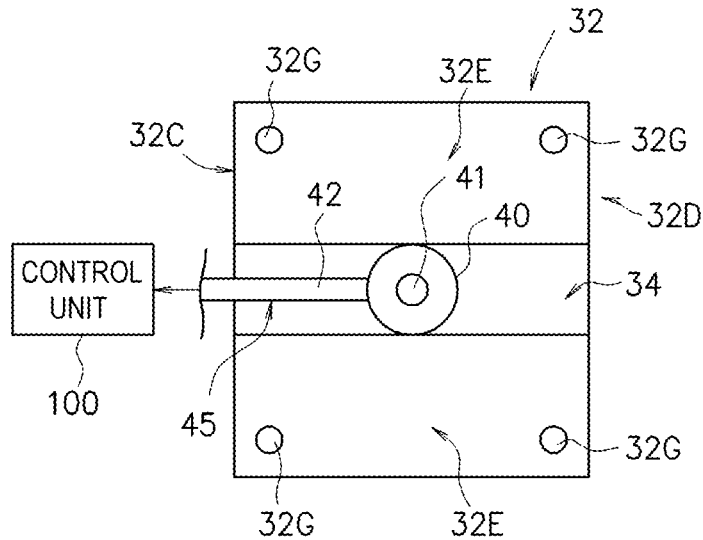
FIGS. 4A, 4B, and 4C are views illustrating an example of a structure of a base portion of the main body portion.
Figure 4B:
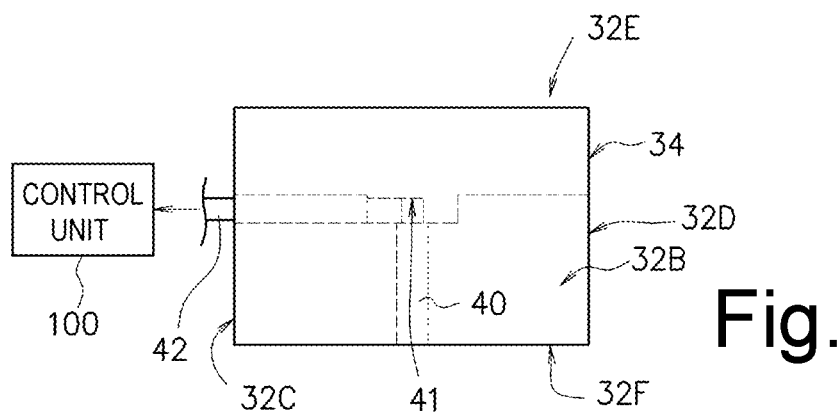
Figure 4C:
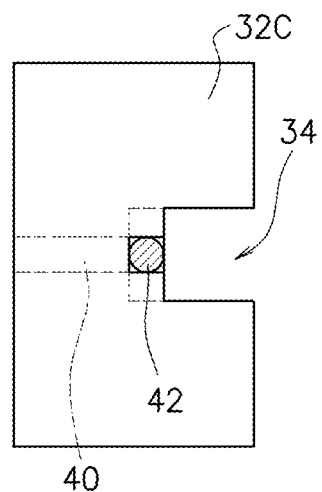

FIG. 3 illustrates the side surface 32D side of the main body portion 31 illustrated in FIG. 2, and an example of the shape of the compressed blood removing tube 11 (the blood feeding tube 12 and the connection tube 19). FIGS. 4A-4C illustrate an example of a structure of the base portion 32 of the main body portion 31. As illustrated in FIG. 3 as an example, the tube mounting recessed portion 34 is formed to have a rectangular cross-sectional shape and is preferably formed to have a square cross section. That is, in the tube mounting recessed portion 34, a width in a height direction and a width in a horizontal direction thereof are formed to be the same distance L. Meanwhile, the blood removing tube 11 (the blood feeding tube 12 and the connection tube 19) illustrated in FIG. 3 has a normal circular cross section.

An external dimension (diameter of the outer circumference) D of the blood removing tube 11 (e.g., the blood feeding tube 12 and the connection tube 19) in a vertical direction and a transverse direction is set to be greater than the width L of the tube mounting recessed portion 34. In this way, the reason that the external dimension D of the blood removing tube 11 (the blood feeding tube 12 and the connection tube 19) in the vertical direction and the transverse direction is set to be greater than the width L of the tube mounting recessed portion 34 is as follows. It is because in a state in which the blood removing tube 11 (the blood feeding tube 12 and the connection tube 19) is removably fitted inside the tube mounting recessed portion 34, a natural circular cross section of the blood removing tube 11 (the blood feeding tube 12 and the connection tube 19) is elastically deformed into a substantially square cross section inside the tube mounting recessed portion 34 in accordance with the rectangular cross-sectional shape of the tube mounting recessed portion 34.

In this way, if the blood removing tube 11 (the blood feeding tube 12 and the connection tube 19) is mounted inside the tube mounting recessed portion 34 in a state in which a circular cross section thereof is elastically deformed into a substantially square cross section, a substantially flat surface SR is formed in apart of the blood removing tube 11 (the blood feeding tube 12 and the connection tube 19). In addition, a measurement distal portion 41 of the pressure measurement element 40 is disposed in a position of being exposed or protruding inside the tube mounting recessed portion 34. Therefore, in a state in which the blood removing tube 11 (the blood feeding tube 12 and the connection tube 19) is removably fitted inside the tube mounting recessed portion 34, the flat surface SR of the blood removing tube 11 (the blood feeding tube 12 and the connection tube 19) can abut on or come into contact with the measurement distal portion 41 of the pressure measurement element 40 in a manner substantially perpendicular thereto. Therefore, the pressure measurement element 40 can simply, instantaneously, and safely measure the intra-circuit pressure without being in contact with blood when blood in the blood removing tube 11 (the blood feeding tube 12 and the connection tube 19) circulates.

In order to obtain the desired deformation of tube 11 in FIG. 3, distance L corresponding to the width and height of recessed portion 34 is in a preferred range of L=πD×0.9÷4 to L=πD×1.1÷4 (e.g., from about 70% to about 86% of outside diameter D). In one example embodiment, a tube having an inner diameter of 9.5 mm and an outside diameter of 14.2 mm was used with a recessed channel of width/height L=10 mm. In a case where the width L of the mounting recessed portion is greater than 14.2 mm with respect to the external dimension D of the tube of 14.2 mm, the pressure cannot be appropriately measured. In addition, in a case where the width L of the mounting recessed portion is smaller than 10.0 mm, a measurable range for the pressure sensor is narrowed or a compression pressure is excessively applied, so that it is unlikely to accurately measure the blood pressure. Here, in the recessed portion 34 described in FIG. 3 and the like, the cross-sectional shape of the recessed portion is not limited to a square shape or a rectangular shape. When the tube is accommodated, if the recessed portion has a predetermined accommodation depth, and the flat surface SR described in FIG. 3 or a convex portion caused by the vertically squashed tube can be formed, the cross-sectional system of the recessed portion may have a semicircular shape or an elliptical shape.

Returning to FIG. 2, the lid portion 33 illustrated in FIG. 2 is a plate-shaped member having a size in accordance with the size of the front surface 32E of the base portion 32. The lid portion 33 covers the front surface 32E side of the base portion 32 to cover the opening part of the tube mounting recessed portion 34, so that the lid portion 33 and the base portion 32 form the tube mounting recessed portion 34 having a square cross section. The lid portion 33 has four hole portions 33A, and the front surface 32E of the base portion 32 similarly has four female screw portions 32G. Screws 33H are screwed into the four female screw portions 32G through the four hole portions 33A, so that the lid portion 33 covers the front surface 32E of the base portion 32 and the opening part of the tube mounting recessed portion 34 is covered as illustrated in FIG. 3.

In this way, when the lid portion 33 covers the opening part of the tube mounting recessed portion 34, a circular cross section of the blood removing tube 11 (the blood feeding tube 12 and the connection tube 19) can maintain a state of being elastically deformed into a substantially square cross section inside the tube mounting recessed portion 34. Therefore, the blood removing tube 11 (e.g., the blood feeding tube 12 and the connection tube 19) acquires the substantially flat surface SR, and the substantially flat surface SR comes into contact with the measurement distal portion 41 of the pressure measurement element 40 in a manner substantially perpendicular thereto. Then, the pressure measurement element 40 accurately measures the intra-circuit pressure when blood circulates in the blood removing tube 11 (the blood feeding tube 12 and the connection tube 19).

As described above, the main body portion 31 has a simple structure of only fixing the lid portion 33 to the base portion 32 in which the blood removing tube 11 (the blood feeding tube 12 and the connection tube 19) fitted, by using the screw 33H. Therefore, as illustrated in FIG. 1, the removable pressure sensor 30 can be simply attached in any position of the mounting position W1 in an intermediate part of the blood removing tube 11 of the circulation circuit 1R, the mounting position W2 in an intermediate part of the blood feeding tube 12 of the circulation circuit 1R, and mounting position W3 in an intermediate part of the connection tube 19. Furthermore, the removable pressure sensor 30 can also be simply detached.

Incidentally, the material of the main body portion 31 illustrated in FIGS. 2 and 3 need only be a material having sufficient rigidity such that the blood removing tube 11, the blood feeding tube 12, and the connection tube 19 can be elastically deformed in a fitted state. The main body portion 31 can be made of metal or plastic. For example, the main body portion 31 can be made of metal such as aluminum or stainless steel. Alternatively, the main body portion 31 can be made of plastic such as polyacetal (POM), polybutylene terephthalate (PBT), and polyethylene terephthalate (PET). The material is not particularly limited. If the main body portion 31 is made of transparent plastic, an operator can visually check the fitted state of the blood removing tube 11, the blood feeding tube 12, and the connection tube 19 through the main body portion 31, thereby being more preferable.

As illustrated in FIGS. 1 and 2, the pressure measurement element 40 is electrically connected to the control unit 100, and the intra-circuit pressure signal SS measured by the pressure measurement element 40 is transmitted to the control unit 100 via the signal line 42. FIG. 4A is a front view of the base portion 32, FIG. 4B is a bottom view of the base portion 32, and FIG. 4C is a side view of the base portion 32. As illustrated in FIG. 4A, the signal line 42 connected to the pressure measurement element 40 is guided out to the outside from the base portion 32 in a state of being fitted in a guide groove 45.

In regard to the material of the pressure measurement element 40 illustrated in FIGS. 2 to 4, examples thereof include an element employing semiconductor silicon as a material, an element using Ni—Cu alloy, and an element using ceramic. For example, it is preferable to use the pressure measurement element 40 employing semiconductor silicon as a material. Examples of the pressure measurement element employing semiconductor silicon as a material include a diffusion type, a film forming type, and an electrostatic capacity type. In the diffusion type, for example, a Si diaphragm is used as a displacement base material, and an output element is a strain gauge. In the film forming type, for example, a SUS diaphragm is used as the displacement base material, and the output element is the strain gauge. In the electrostatic capacity type, for example, a Si diaphragm is used as the displacement base material, and the output element is an Al film. In addition, as the pressure measurement element, other than the pressure measurement elements described above, a load cell can be used.

Figure 5:
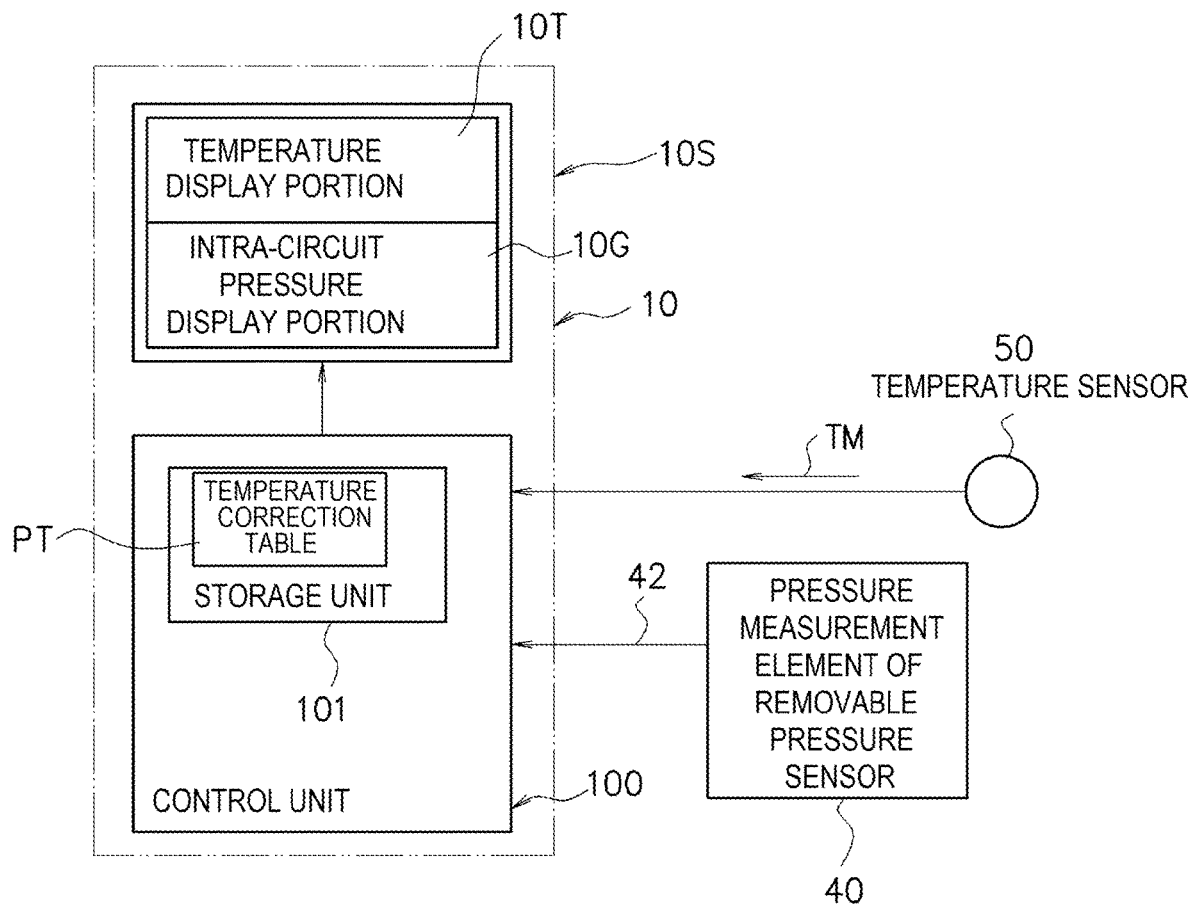
FIG. 5 is a view illustrating a controller, a pressure measurement element, and a temperature sensor.

FIG. 5 illustrates an example of electrical connection among the controller 10, the pressure measurement element 40, and a temperature sensor 50. As illustrated in FIG. 5, the signal line 42 of the pressure measurement element 40 is electrically connected to the control unit 100 of the controller 10. In addition, the temperature sensor 50 is electrically connected to the control unit 100. The temperature sensor 50 measures a temperature change in an environment in which the extracorporeal circulator 1 illustrated in FIG. 1 is set, and the temperature sensor 50 notifies the control unit 100 of environmental temperature information TM. As illustrated in FIG. 5, the controller 10 has a display portion 10S such as a liquid crystal display device, and the display portion 10S has a temperature display portion 10T and an intra-circuit pressure display portion 10G.

The control unit 100 illustrated in FIG. 5 has a storage unit 101. The storage unit 101 stores a temperature correction table PT for correcting an elastic change caused by a temperature change in the blood removing tube 11 (the blood feeding tube 12 and the connection tube 19) which is in use. If the blood removing tube 11 (the blood feeding tube 12 and the connection tube 19) is elastically changed due to a temperature change in the located environment, the intra-circuit pressure during blood circulation through the inside of the blood removing tube 11 (the blood feeding tube 12 and the connection tube 19) subtly changes when an extracorporeal circulation operation or an auxiliary circulation operation is performed.

Figure 6:
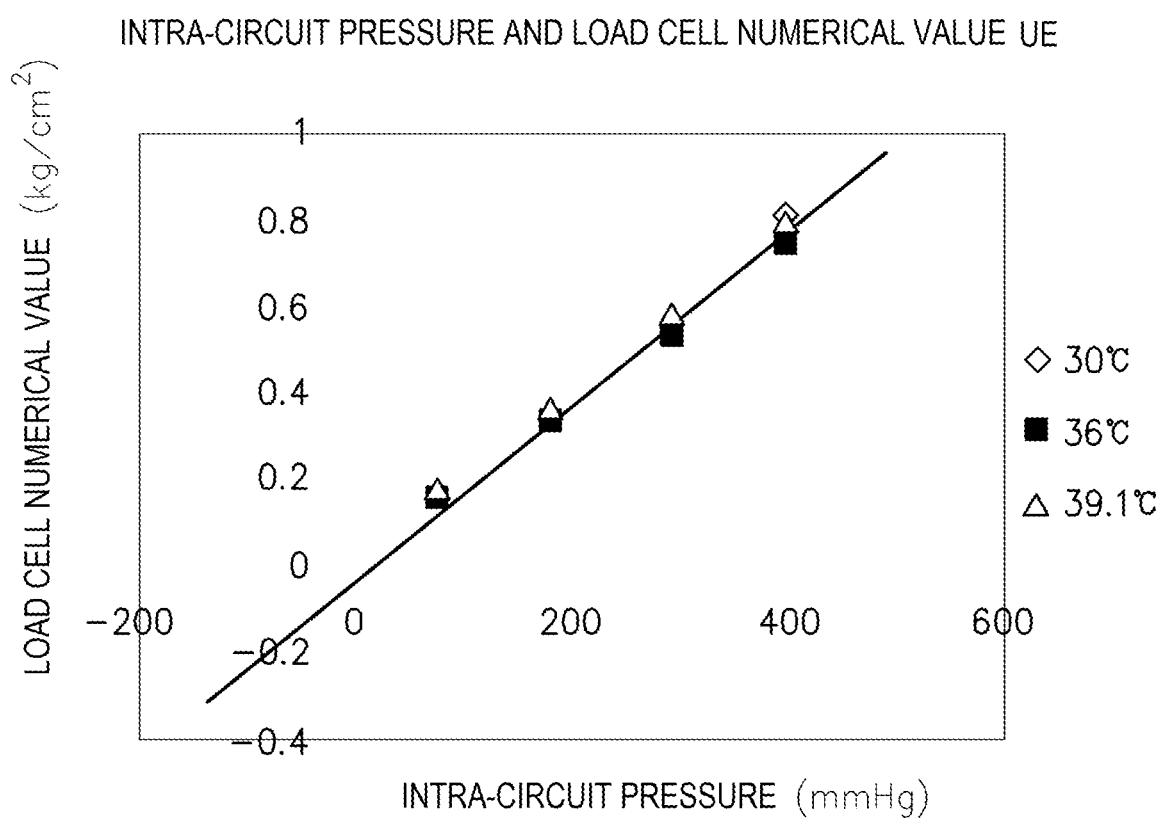
FIG. 6 is a view illustrating an example of a relationship between a load cell numerical value (kg/cm2) and an intra-circuit pressure (mmHg) in a case where a load cell is used as the pressure measurement element.

Therefore, even if the temperature of the located environment changes, the control unit 100 can acquire a more accurate intra-circuit pressure during blood circulation by correcting the value of the intra-circuit pressure during blood circulation in the blood removing tube 11 (the blood feeding tube 12 and the connection tube 19) based on the temperature correction table PT. The intra-circuit pressure display portion 10G of the controller 10 can display the intra-circuit pressure. In addition, the temperature display portion 10T can display the temperature of the environment. FIG. 6 illustrates an example of a relationship between a load cell numerical value (kg/cm2) and an intra-circuit pressure (mmHg) in a case where a load cell is used as the pressure measurement element. FIG. 6 illustrates that the intra-circuit pressure slightly changes in a tube such as the blood removing tube 11 (the blood feeding tube 12 and the connection tube 19) due to an elastic change of the tube caused by a change in the environmental temperature.

As described above, in the first embodiment of the present invention, if the tube has a constant external dimension, an operator can simply and removably mount the removable pressure sensor 30 in any position, and it is possible to simply, instantaneously, and safely measure the intra-circuit pressure of blood circulating in the circuit during extracorporeal circulation or auxiliary circulation in a treatment theater or a surgical theater. During circulation of blood, the controller 10 can check a trend of a change in the intra-circuit pressure (tendency of a change in pressure) rather than detecting the absolute value of the intra-circuit pressure inside the tube 11 (12, 19). As already described, in FIG. 1, the removable pressure sensor 30 is mounted in the mounting position W1 in an intermediate part of the blood removing tube 11 of the circulation circuit 1R, and when an extracorporeal circulation operation or an auxiliary circulation operation is performed, it is possible to measure the intra-circuit blood removing pressure during blood circulation through the inside of the blood removing tube 11 without being in contact with blood. Accordingly, when blood is removed from the patient P, the controller 10 can determine a trend of a change in a blood removing state (tendency of a change in pressure) of the patient P.

In addition, the removable pressure sensor 30 is mounted in the mounting position W2 in an intermediate part of the blood feeding tube 12 of the circulation circuit 1R, and when an extracorporeal circulation operation or an auxiliary circulation operation is performed, it is possible to measure the intra-circuit blood feeding pressure during blood circulation through the inside of the blood feeding tube 12 without being in contact with blood. Accordingly, when blood is fed into the patient P, the controller 10 can detect an undesirable condition of the artificial lung 2 or a trend of a change in a blood feeding state (tendency of a change in pressure) of the patient P. Moreover, the removable pressure sensor 30 can be mounted in the mounting position W3 in an intermediate part of the connection tube 19, and when an extracorporeal circulation operation or an auxiliary circulation operation is performed, it is possible to measure the intra-circuit blood feeding pressure during blood circulation through the inside of the connection tube 19 without being in contact with blood when blood is fed by the centrifugal pump 3. Accordingly, the controller 10 can detect a trend of a change in an operation (tendency of a change in pressure) of the centrifugal pump 3 in the circulation circuit 1R.

Second Embodiment

Figure 7A:
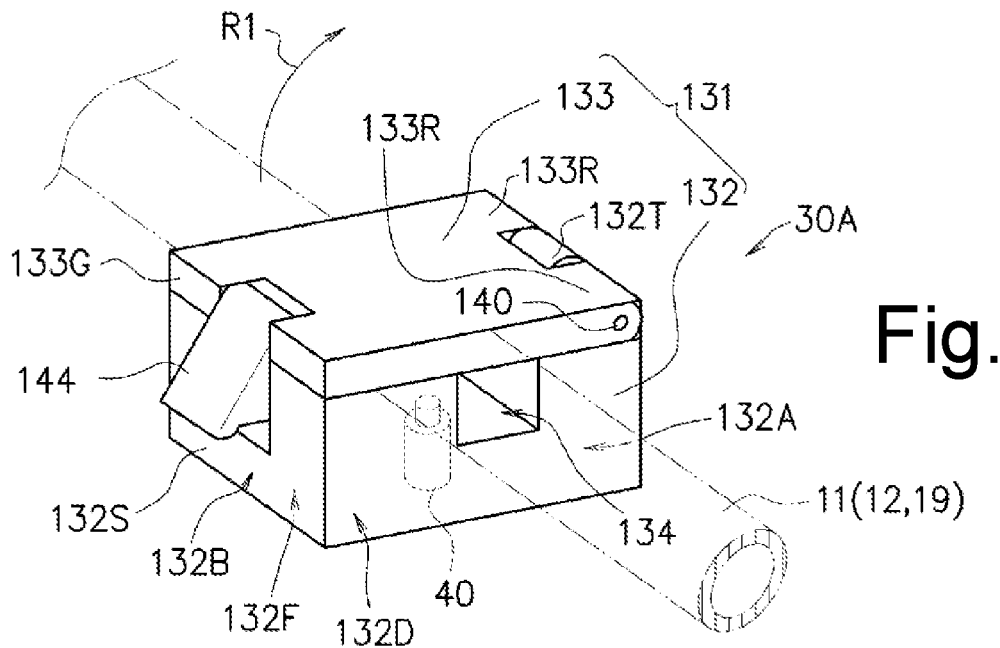
FIGS. 7A and 7B are perspective views illustrating a removable pressure sensor of a second embodiment of the present invention in a closed position and an open position, respectively.
Figure 7B:
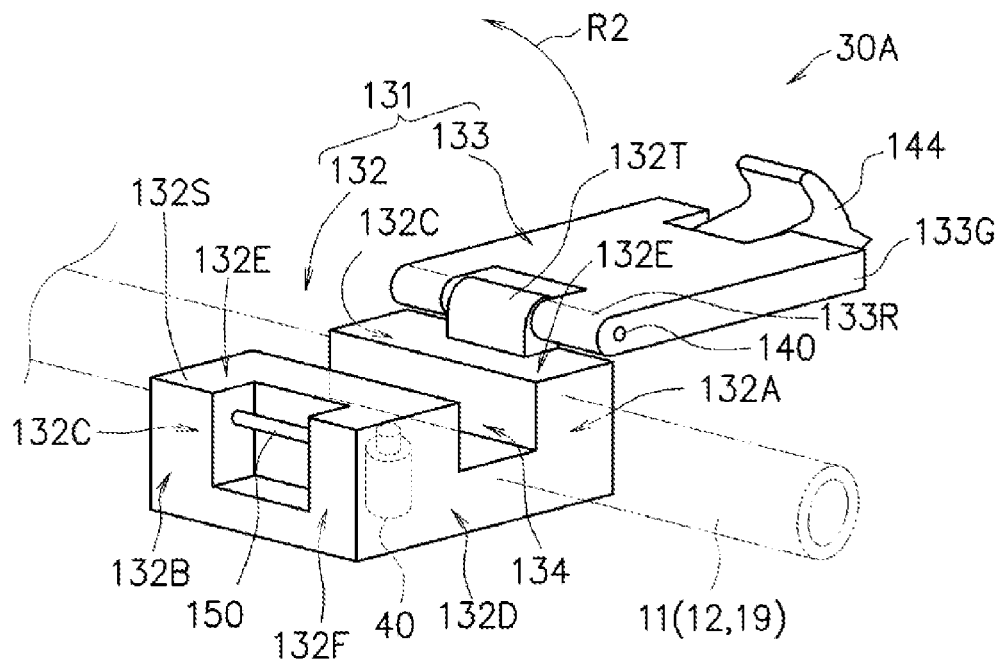

Next, a removable pressure sensor 30A of a second embodiment of the present invention will be described with reference to FIGS. 7A and 7B. FIGS. 7A and 7B are perspective views illustrating the removable pressure sensor 30A of the second embodiment of the present invention. As illustrated in FIG. 7, the removable pressure sensor 30A has a main body portion 131 and the pressure measurement element 40 which is attached to the main body portion 131. The main body portion 131 has a base portion 132 and a lid portion 133. The material of the main body portion 131 may be metal similar to that of the first embodiment or may be plastic.

FIG. 7(A) illustrates a state in which the lid portion 133 is closed with respect to the base portion 132, and FIG. 7(B) illustrates a state in which the lid portion 133 is opened from the base portion 132. As illustrated in FIG. 7(B), for example, the base portion 132 is a rectangular parallelepiped solid member and has a tube mounting recessed portion 134. The base portion 132 has an upper surface 132A, a lower surface 132B, right and left side surfaces 132C, 132D, a front surface 132E, and a rear surface 132F. The tube mounting recessed portion 134 is formed from the front surface 132E side toward the rear surface 132F side. The tube mounting recessed portion 134 is formed from the left side surface 132C side leading to the right side surface 132D.

Meanwhile, as illustrated in FIGS. 7(A) and 7(B), the lid portion 133 is attached to the base portion 132 in a manner of being able to be opened and closed. In more detail, one end portion 133R of the lid portion 133 is rotatably interlocked on one end portion 132T side of the base portion 132 via a hinge portion 140. Accordingly, the lid portion 133 can be opened in an R1 direction or closed in an R2 direction with respect to the base portion 132. If the lid portion 133 and the base portion 132 are made of transparent plastic, an operator has the ability to visually check the holding state of the blood removing tube 11 (the blood feeding tube 12 and the connection tube 19) mounted inside the tube mounting recessed portion 134.

A hook 144 is attached to the other end portion 133G of the lid portion 133. As illustrated in FIG. 7(B), a rod-shaped fastening member 150 is attached to the other end portion 132S of the base portion 132. As illustrated in FIG. 7(A), when the hook 144 engages with the fastening member 150, the lid portion 133 can close the opening part of the tube mounting recessed portion 134 in a manner of latching to the front surface 132E of the base portion 132. In this way, in the second embodiment illustrated in FIG. 7, an operator can simply and reliably close the tube mounting recessed portion 134 by only hooking the hook 144 of the lid portion 133 to the fastening member 150 of the base portion 132 without using a screw. Therefore, when extracorporeal circulation or auxiliary circulation is performed, the removable pressure sensor 30A can simply, instantaneously, and safely measure the intra-circuit pressure of blood circulating in the circuit.

In the related art, in order to check a change in the intra-circuit pressure during extracorporeal circulation or auxiliary circulation, an operator of the extracorporeal circulator 1 needs to provide a bifurcated portion for a pressure sensor in a tube and to fill the inside of the bifurcated portion with a liquid (blood). Since this filling work is troublesome work, the operation cannot simply, instantaneously, and safely measure the intra-circuit pressure. In contrast, in the embodiment of the present invention, during extracorporeal circulation or auxiliary circulation, there is no need to perform troublesome work of providing a bifurcated portion for a pressure sensor in the tube and filling the inside of the bifurcated portion with a liquid (blood), as in the related art. Therefore, during extracorporeal circulation or auxiliary circulation, if the tube has a constant external dimension along its length, the removable pressure sensor 30 (30A) can be simply, instantaneously, safely, and removably mounted in any position, and it is possible to check a change in the intra-circuit pressure.

In the embodiments of the present invention, if the blood removing tube 11 (the blood feeding tube 12 and the connection tube 19) is mounted inside the tube mounting recessed portion 34 in a state in which a circular cross section thereof is elastically deformed into a substantially square cross section, the blood removing tube 11 (the blood feeding tube 12 and the connection tube 19) can acquire a substantially flat surface R. Therefore, since the substantially flat surface R can abut on or come into contact with the distal portion 41 of the pressure measurement element 40 in a manner substantially perpendicular thereto, the pressure measurement element 40 can more accurately measure the intra-circuit pressure of the blood removing tube 11 (the blood feeding tube 12 and the connection tube 19).

As described above, the removable pressure sensor 30 (30A) of the embodiment of the present invention is a removable pressure sensor which can be removably mounted in a middle part of the elastically deformable tube 11 (12, 19) for transferring blood as an example of a liquid. For example, the removable pressure sensor 30 includes the main body portion 31 and the pressure measurement element 40 which is disposed in the main body portion 31. The main body portion 31 has the base portion 32 having the tube mounting recessed portion 34 in which a middle part of the tube 11 (12, 19) is removably fitted, the tube is elastically deformed, and the pressure measurement element 40 measures a circuit pressure of a liquid inside the tube 11 (12, 19); and the lid portion 33 holding the tube 11 (12, 19) inside the tube mounting recessed portion 34 by closing the tube mounting recessed portion 34 of the base portion. The tube mounting recessed portion 34 has a rectangular cross section, and the width L of the rectangular cross section is set to be smaller than the external dimension D of the tube.

Accordingly, the pressure measurement element 40 can measure the circuit pressure of the liquid inside the tube 11 (12, 19) by only fitting the intermediate part of the tube 11 (12, 19) in the tube mounting recessed portion 34. The tube mounting recessed portion 34 has a rectangular cross section, and the width L of the rectangular cross section is set to be smaller than the external dimension D of the tube. Accordingly, the tube mounting recessed portion 34 can form the cross-sectional shape of the tube into a substantially rectangular cross-sectional shape by compressing the tube to be elastically deformed in accordance with the rectangular shape of the tube mounting recessed portion 34. Therefore, the pressure measurement element 40 can simply, instantaneously, and safely measure the intra-circuit pressure of the liquid circulating in the circuit by abutting on the flat surface SR formed in a part of the tube. That is, in the embodiment of the present invention, since there is no need to fill a liquid flow path, which is a bifurcated portion with respect to the tube, and a liquid chamber with a liquid as in the related art, the intra-circuit pressure of the circulating liquid can be simply and instantaneously measured. Since there is no bifurcated portion in the tube, a thrombus or the like is not generated. Accordingly, the intra-circuit pressure of the circulating liquid can be safely measured.

The rectangular cross section of the tube mounting recessed portion 34 is a substantially square cross section, and the pressure measurement element 40 is disposed in a position corresponding to the tube 11 (12, 19) which is elastically deformed and is held in the tube mounting recessed portion 34. Accordingly, the tube mounting recessed portion 34 having a substantially square cross section can form the tube 11 (12, 19) to have a substantially square shape by causing the tube to be elastically deformed in accordance with the substantially square cross section of the tube mounting recessed portion 34. Therefore, the flat surface SR can be formed in a part of the tube, so that the pressure measurement element 40 can accurately measure the intra-circuit pressure of the liquid circulating in the circuit by abutting on the formed flat surface SR.

The removable pressure sensor includes the temperature sensor 50 which measures a temperature of an environment in which the tube is positioned; and the control unit 100 which acquires temperature information of the environment from the temperature sensor 50, acquires a circuit pressure of the liquid inside the tube from the pressure measurement element 40, and corrects the circuit pressure of the liquid inside the tube measured by the pressure measurement element, in accordance with a value of the temperature. Accordingly, since the circuit pressure of the liquid inside the tube 11 (12, 19) can be corrected in accordance with the value of the temperature of the environment in which the tube 11 (12, 19) is positioned, even if the temperature of the environment changes, it is possible to acquire a more accurate circuit pressure.

The lid portion 33 is attached to the base portion 32 in a manner of being able to be opened and closed, and the lid portion 33 holds the tube 11 (12, 19) inside the tube mounting recessed portion 34 when the lid portion 33 closes the tube mounting recessed portion 34 of the base portion 32. Accordingly, an operator can more simply and instantaneously close the tube mounting recessed portion by using the lid portion 33, so that the removable pressure sensor 30 can be easily attached and detached with respect to the tube 11 (12, 19).

The extracorporeal circulator 1 provided with a removable pressure sensor of the embodiment of the present invention includes the removable pressure sensor 30 which is removably mounted in a middle part of the elastically deformable tube 11 (12, 19) for transferring a liquid when the liquid is in extracorporeal circulation. The removable pressure sensor 30 includes the main body portion 31 and the pressure measurement element 40 which is disposed in the main body portion 31. The main body portion 31 has the base portion 32 having the tube mounting recessed portion 34 in which the middle part of the tube 11 (12, 19) is removably fitted, the tube is elastically deformed, and the pressure measurement element 40 measures the circuit pressure of the liquid inside the tube 11 (12, 19); and the lid portion 33 holding the tube inside the tube mounting recessed portion by closing the tube mounting recessed portion 34 of the base portion 32. The tube mounting recessed portion 34 has a rectangular cross section, and the width L of the rectangular cross section is set to be smaller than the external dimension D of the tube. Accordingly, the pressure measurement element 40 can measure the circuit pressure of the liquid inside the tube 11 (12, 19) by only fitting the middle part of the tube 11 (12, 19) in the tube mounting recessed portion 34.

The tube mounting recessed portion 34 has a rectangular cross section, and the width L of the rectangular cross section is set to be smaller than the external dimension D of the tube. Accordingly, the tube mounting recessed portion 34 can form the circular cross-sectional shape of the tube into a substantially rectangular cross-sectional shape by causing the tube to be elastically deformed in accordance with the rectangular shape of the tube mounting recessed portion 34. Therefore, the pressure measurement element 40 can simply, instantaneously, and safely measure the intra-circuit pressure of the liquid circulating in the circuit by abutting on the flat surface SR formed in a part of the tube. That is, in the embodiment of the present invention, since there is no need to fill a liquid flow path, which is a bifurcated portion with respect to the tube, and a liquid chamber with a liquid as in the related art, the intra-circuit pressure of the circulating liquid can be simply and instantaneously measured. Since there is no bifurcated portion in the tube, a thrombus or the like is not generated. Accordingly, the intra-circuit pressure of the circulating liquid can be safely measured.

The present invention is not limited to the above-described embodiments and various changes can be made without departing from the scope of Claims. Each of the above-described embodiments of the present invention can be combined in any manner. Each of the configurations in the embodiments can be partially omitted or can be combined in any manner to be different from that described above.

For example, the removable pressure sensor 30 (30A) is removably mounted in the tubes 11, 12, and 19 of the extracorporeal circulator 1 performing extracorporeal circulation or auxiliary circulation of blood as an example of a liquid. However, without being limited thereto, the removable pressure sensor 30 (30A) may also be removably mounted in a tube for transferring a liquid, in an apparatus in a field other than an extracorporeal circulator for blood circulation.

In addition, in the recessed portions 34 and 134 described in FIG. 3 and the like, the cross-sectional shape of the recessed portion is not limited to a square shape or a rectangular shape. When the tube is accommodated, if the recessed portion has a predetermined accommodation depth, and the flat surface SR described in FIG. 3 can be formed, the cross-sectional system of the recessed portion may have a semicircular shape or an elliptical shape.

What is claimed is:

1. A pressure sensor assembly configured to be removably mounted in an intermediate part of an elastically deformable tube for transferring a liquid, the pressure sensor assembly comprising:
   a main body portion; and
   a pressure measurement element that is disposed in the main body portion;
   wherein the main body portion comprises:
      a base portion having a tube mounting recessed portion with a cross-sectional width L configured to removably receive the intermediate part of the tube so as to cause the tube to be elastically deformed, wherein the pressure measurement element has a surface bordering the tube mounting recessed portion to cause a pressure of the liquid inside the tube to be transmitted to the pressure measurement element; and
      a lid portion configured to hold the tube inside the tube mounting recessed portion in a state in which the tube mounting recessed portion of the base portion is closed;
   wherein the width L of a cross section of the tube mounting recessed portion is configured to be smaller than an outside diameter D of the tube, such that L is within a range from L=πD×0.9÷4 to L=πD×1.1÷4; and
   wherein the tube mounting recessed portion has a substantially square cross section, wherein the pressure measurement element is disposed in a side of the tube mounting recessed portion against which the tube which is elastically deformed when held by the lid portion in the tube mounting recessed portion, wherein a width of the substantially square cross section is set to be smaller than the outside diameter D of the tube so that a substantially flat surface is formed in the tube at the pressure measurement element.

2. The removable pressure sensor according to claim 1, further comprising:
   a temperature sensor that measures a temperature of an environment in which the tube is positioned; and
   a control unit that acquires temperature information of the environment from the temperature sensor, acquires the circuit pressure of the liquid inside the tube from the pressure measurement element, and corrects the circuit pressure of the liquid inside the tube measured by the pressure measurement element, in accordance with a value of the temperature.

3. The removable pressure sensor according to claim 1:
   wherein the lid portion is attached to the base portion in a manner of being selectably opened and closed, and the lid portion holds the tube inside the tube mounting recessed portion in a state in which the lid portion closes the tube mounting recessed portion of the base portion.

4. An extracorporeal circulator system for treating blood of a patient, comprising:
   an elastically deformable tube for transferring the blood in extracorporeal circulation; and
   a removable pressure sensor comprising a main body portion and a pressure measurement element that is disposed in the main body portion;
   wherein the main body portion comprises:
      a base portion having a tube mounting recessed portion with a cross-sectional width L configured to removably receive an intermediate part of the tube so as to cause the tube to be elastically deformed, wherein the pressure measurement element has a surface bordering the tube mounting recessed portion to cause a pressure of the blood inside the tube to be transmitted to the pressure measurement element; and
      a lid portion configured to hold the tube inside the tube mounting recessed portion in a state in which the tube mounting recessed portion of the base portion is closed;
   wherein the width L of a cross section of the tube mounting recessed portion is configured to be smaller than an outside diameter D of the tube, such that L is within a range from L=πD×0.9÷4 to L=πD×1.1÷4; and
   wherein the tube mounting recessed portion has a substantially square cross section, wherein the pressure measurement element is disposed in a side of the tube mounting recessed portion against which the tube which is elastically deformed when held by the lid portion in the tube mounting recessed portion, wherein a width of the substantially square cross section is set to be smaller than the outside diameter D of the tube so that a substantially flat surface is formed in the tube at the pressure measurement element.

\* \* \* \* \*